United States Patent
Farnes et al.

(10) Patent No.: US 7,074,168 B1
(45) Date of Patent: Jul. 11, 2006

(54) SYSTEM FOR HUMAN PHYSICAL EVALUATION AND ACCOMPLISH IMPROVED PHYSICAL PERFORMANCE

(76) Inventors: Larry D. Farnes, 4430 Paradise Ave. West, University Place, WA (US) 98466; Lee Caton, 5912-B Hannah-Pierce Rd. West, University Place, WA (US) 98466; Jon Mortensen, 10116 - 102nd Ave. Ct. West, Lakewood, WA (US) 98498

( * ) Notice: Subject to any disclaimer, the term of this patent is extended or adjusted under 35 U.S.C. 154(b) by 868 days.

(21) Appl. No.: 10/217,935

(22) Filed: Aug. 12, 2002

Related U.S. Application Data

(60) Provisional application No. 60/311,479, filed on Aug. 10, 2001.

(51) Int. Cl.
*A63B 21/00* (2006.01)

(52) U.S. Cl. .............................. 482/148; 482/8; 482/900

(58) Field of Classification Search ................. 482/1–9, 482/148, 900–902; 434/247
See application file for complete search history.

(56) References Cited

U.S. PATENT DOCUMENTS

| | | |
|---|---|---|
| 4,631,676 A | 12/1986 | Pugh |
| 4,665,928 A | 5/1987 | Linial et al. |
| 4,912,638 A | 3/1990 | Pratt |
| 5,368,042 A | 11/1994 | O'Neal et al. |
| 5,375,610 A | 12/1994 | LaCourse et al. |
| 5,462,065 A | 10/1995 | Cusimano |
| 5,511,789 A | 4/1996 | Nakamura |
| 5,551,445 A | 9/1996 | Nashner |
| 5,553,846 A | 9/1996 | Frye et al. |
| 5,573,012 A | 11/1996 | McEwan |
| 5,638,300 A | 6/1997 | Johnson |
| 5,754,121 A | 5/1998 | Ward et al. |
| 5,791,351 A | 8/1998 | Curchod |
| 5,826,578 A | 10/1998 | Curchod |
| 5,907,819 A | 5/1999 | Johnson |
| 5,919,149 A | 7/1999 | Allum |
| 5,961,474 A | 10/1999 | Reis |
| 5,980,429 A | 11/1999 | Nashner |
| 5,984,684 A | 11/1999 | Brostedt et al. |
| 5,984,810 A | 11/1999 | Frye et al. |
| 6,032,530 A | 3/2000 | Hock |
| 6,050,962 A | 4/2000 | Kramer et al. |
| 6,050,963 A | 4/2000 | Johnson et al. |
| 6,056,671 A * | 5/2000 | Marmer .......................... 482/8 |
| 6,059,576 A * | 5/2000 | Brann ......................... 434/247 |
| 6,067,986 A | 5/2000 | Kluger et al. |
| 6,120,467 A | 9/2000 | Schallhorn |
| 6,626,800 B1 * | 9/2003 | Casler .......................... 482/8 |

* cited by examiner

*Primary Examiner*—Glenn E. Richman
(74) *Attorney, Agent, or Firm*—Robert B. Hughes; Hughes Law Firm, PLLC

(57) ABSTRACT

A system for improving either or both the physical well-being and physical performance of a person, such as in day-to-day activities or sports-related activities. The person's skeletal and muscular characteristics are assessed relative to such things as flexibility, movement, and strength, and the person's performance characteristics relating to an optimized performance of a task or a sports-related activity (e.g. golf swing) are determined. By matching the differences in the person's physical characteristics and performance characteristics, an optimized physical remedial course can be initiated, as well as a remedial course in improving the physical performance related more to learned defects in performance.

3 Claims, 5 Drawing Sheets

SYSTEM FOR HUMAN PHYSICAL EVALUATION AND ACCOMPLISH IMPROVED PHYSICAL PERFORMANCE

RELATED APPLICATIONS

This application claims priority benefit of U.S. Ser. No. 60/311,479, filed Aug. 10, 2001.

BACKGROUND OF THE INVENTION a) Field of the Invention

The present invention relates to the physical well-being and/or performance of a person and how to improve the same. More specifically, it relates to a system by which the physical performance and characteristics of a person are ascertained, quantified, and evaluated so that these can form a basis of a program for a person to achieve selected goals. These can be remedial related goals, more specific goals directed toward improved performance, such as in athletic performance, or more general goals of being able to enjoyably and comfortably function in various physical functions or activities, with all of these contributing to the person's overall well-being.

GENERAL BACKGROUND INFORMATION

Within the broad umbrella of "personal well-being", we find a number of basic elements, each of which in itself is a rather broad category with its own subcategories. For purposes of providing an overall perspective for the present invention, we could place these in five categories:

(a) Basic Health Care

The item which would commonly first come to mind is basic health care. Very few of us go through life without having some of the usual childhood diseases, a damaged joint, tendon or bone, high blood pressure, etc., and these often require medical attention.

(b) Basic Health Habits

Related to basic health care is the second item, which includes prophylactic measures in adopting good physical health habits in day-to-day living. This includes such things as regular brushing of the teeth, basic sanitary steps (e.g. washing your hands frequently, food being handled properly), flue shots, dental checkups, etc.

(c) Proper Diet

This subject occupies such a large part of the attention of our modern society that it deserves to be in a category by itself. If one is to read a book written thirty years ago about proper diet, and then compare this to the more recent volumes on the subject, there would be found many differences. Further, we have the growing emphasis on the dietary supplements, such as the significant recent developments in what is termed the "antioxidant revolution" where (particularly if a person's body is under stress) larger amounts of these antioxidants are recommended to improve the immune system, diminish the probabilities of debilitating cardiovascular effects, etc. This, and good physical health habits, of course, relate back to the first above-mentioned item of maintaining basic health.

(d) Mental, Emotional, Psychological, and Spiritual Well-Being

It should be noted that the term "spiritual well-being" is being used in a broad sense. This category starts at one end of psychiatry and extends into such things as counseling, motivational programs, religion, philosophy, etc. There are numerous books, magazines, etc., which relate to all of these, directed to adding meaning, happiness, motivation, energy, and goals to a person's day-to-day living.

(e) Physical Activities and Physical Conditioning.

This is the category with which the present invention is primarily concerned. Basically, in the context of the present invention this fifth category relates to the person's skeletal, muscular, and cardiovascular condition, as well as the characteristics and functioning of the person's body in a wide variety of physical activities, and also a variety of other related subjects.

All of these items 1–5 interrelate with one another in a synergistic fashion. For example, good health habits and activities in any one of those categories in turn generally has beneficial effects on most or all of the others. For the moment, let us turn our attention to the fifth category of Physical Activities and Physical Condition, and dwell for a few moments on how this relates to the first four categories.

First, it is generally accepted by practitioners in the field of health care that a certain amount of physical activity will generally contribute to the person's basic health. For example, it can relate to the alleviation of various physical ailments, such as osteoporosis, cardiovascular problems, high blood pressure, etc.).

With regard to the interaction within the second item, when a person has a more or less regular routine of physical activity, this in turn becomes part of his overall pattern of living, and this collection of habits reinforce one another in keeping a person in this pattern.

With regard to the third item (proper diet), physical activity will burn unwanted calories. In addition, when a person has a pattern of regular physical activity, he (she) is more likely to be more health conscious and is more likely to follow a healthy diet.

It may be that physical activity makes its most significant contribution in the fourth category of mental, emotional, psychological, and spiritual well-being. Physical activity can be a recreational outlet to give someone a "change of pace", which will enable a person to engage more effectively in other day-to-day activities not related to physically active endeavors. Further, many physical activities involve social contact with other people. In some activities there are aspects of teamwork, sometimes energizing competition (in active sports), or simply getting a change of environment.

It is believed that a clearer understanding of the present invention will be obtained by first discussing rather generally the overall subject of physical condition and physical activities as these relate to overall well-being, and then discuss the system and methods of the present invention.

Let us now first discuss some of the main components that relate to physical well-being in our society. When we talk about physical activity, this obviously includes walking, running, bicycling, sports, and exercise. However, this category of physical activities goes beyond that, and includes physical activities in the workplace (e.g. construction labor, such things as yard work, moving furniture around the house, etc.

One aspect of physical well-being is the problems encountered in being able to perform certain physical tasks. Very few people who have been physically active will go through life without having some sort of physical ailment, such as a dislocation in the back, a tennis elbow, a pulled hamstring, problem with the Achilles tendon in running, etc. Some of these could be work-related ailments that impair the person's ability to properly perform the job. When these occur, a person will sometimes see a health specialist, whether it be a doctor, physical therapist, chiropractor, or (if the person is on an athletic team) a trainer. The person may simply consult the pharmacist to find some suitable over-the-counter remedy, or maybe pick up random advice from friends who have had (or know others who have had) a similar ailment.

To discuss yet another aspect, for at least the last two or three decades, we have developed a more health-conscious society in terms of participating in fitness clubs where there are a wide variety of exercise machines for most every muscle and motion of the body. Also, these are cardiovascular-related machines (treadmills, stair steppers, Nordic ski machines, rowing machines, etc.). The person working out in a health club will likely want to see some progress, or be satisfied to maintain a level of fitness. Many clubs have trainers who may or may not have had any formal training in physical fitness, but have acquired a fair amount of knowledge simply by trial and error in participating in such activities for a period of time.

At other times, the person will simply start his or her own exercise program and "do what comes naturally", which often depends upon what the person feels like doing that day. A fair number of people (if not most people) who participate regularly in fitness club activities will at some time experience some sort of ailment in a muscle, joint, tendon, etc., which will interrupt at least some phases of the exercise program. Or, it could be some rather annoying ailment that only impairs physical motions.

Then there is this vast area of sports, ranging all the way from highly competitive and high profile sports, to a friendly game of golf, a YMCA basketball league, etc. When a person takes an interest in a sports activity, even if it's a recreational activity where the person might be feeling some frustration in performing more poorly in a certain segment of that sporting activity, whether it be an erratic driver in golf, streaks of wildness in pitching, inability to make free throws (even some of the otherwise remarkable basketball stars such as Wilt Chamberlain and Bill Russell have had trouble in this area), an erratic backhand in tennis, etc. Usually the remedy is that the person seeks advice from someone who has insights in the particular activity. Or, the person simply may try to emulate the athletic movements of the person that has skills in that activity. But that is not necessarily the best remedy.

At this point, it might be helpful to reflect upon the various informational inputs that a person receives relating to these various activities. There is almost what we might call an "overabundance" of information, or what is sometimes referred to as "information pollution" in that we have so much of it that it becomes difficult to sort it out in some meaningful pattern. For example, there are magazines published on most every physical related activity in our modern-day living, whether it be sports, outdoor living, fitness, muscular strength, etc. In the field of golf, for example, there are two publications that have a circulation of over a million (i.e., Golf Digest and Golf Magazine), and there is another magazine entitled "Ladies Golf." There are magazines on running, walking, bicycling, horseback riding, water skiing, surfing, snowboarding, mountain biking, tennis, hiking, etc.

It is with all of this in mind that the program of the present invention was created. Different activities make different demands upon a person's physical abilities. People come in all sizes and shapes, with different characteristics, limitations, strengths, etc. Some of us are limber and agile, while others come close to resembling the tin man in "The Wizard of Oz." Some people are physically strong in some muscle group and lack strength in others. The posture and bone structure may have certain characteristics that lead to certain ailments or limitations, etc. Then the demands of various physical activities, such as requirements of some sports, etc., are rather different. Yet, if a person searches through all of this information, there will be certain "themes" that can be identified and be individualized, and applied to various situations.

SUMMARY OF THE INVENTION

The system and method of improving either or both of physical well-being and physical performance of a person, by first ascertaining quantifiable information about the person's physical characteristics (skeletal and muscular characteristics) and also matching these with a person's performance in performing various tasks. The present system could be applied to various human activities, such as recreational activities, sports activities, or work activities. A specific embodiment of improving a person's golf swing is described by a combination of proper identification of the physical characteristics of the person and/or learned faults in the person's performance of the swing.

The system of the present invention has a number of interrelated components which are described in such a way as to reach into many of the main areas of physical activities and physical condition, and to provide a comprehensive program to "put it all together" and yet individualize it for specific situations. Among the more significant components are the following:

a) Assessing, evaluating, and quantifying a person's overall physical characteristics and capabilities as they relate generally to his/her physical well-being;

b) Utilizing the information of item (a) of the strengths, deficiencies, and areas of desired improvement or correction identified in item (a) above in initiating remedial steps, and/or steps for improvement along with a program for accomplishing certain goals and monitoring the results;

c) Conducting an assessment and analysis of one or more specific activities of a person (e.g. an aspect of an athletic performance), initiating the procedures to improve such performance, and/or achieve other goals and monitoring the same as part of an ongoing program;

d) As part of initiating the procedures of item (c), reviewing the assessment and analysis of the specific physical movements of the person (as specified in item (c) above) and relating this to the information of the basic physical characteristics and the abilities and/or deficiencies of the person, as specified in item (a) above, as a means of improving performance;

e) From the assessment of item (a) and from the program of item (c) and item (d) identifying possible additional remedial steps and/or a remedial program relating to physical characteristics and/or deficiencies, to achieve further improvement of (and/or achieving the other goals relating to) the performance of the physical activity or activities of item (c);

f) Relating to the components of all of items (a) through (e) so that these are combined in a manner to become part of an overall pattern of living.

The system outlined in paragraphs (a) through (f) is rather flexible in that a person can participate in the total program or only in specific parts of it. For example, a person may want to limit his/her participation to achieve a specific goal of optimizing physical well-being as part of a continuing pattern of living.

To discuss more specifically the steps in the method of the present invention in certain preferred embodiments these are the following steps:

a) Ascertaining quantifiable information about the person's physical characteristics relating to:
   i) the person's skeletal characteristics including flexibility and movement, and muscular characteristics including movement, flexibility, and strength;
   ii) the person's performance characteristics in performing physical movements in performing a task or tasks.

b) Then there are established performance standards corresponding to a desired performance level for said task or tasks, and also establishing skeletal and muscular standards corresponding to desired skeletal and muscular characteristics capable of matching the performance standards.

c) The next step is to match the person's skeletal and muscular characteristics with the skeletal and muscular standards and determine skeletal and muscular differences therebetween.

d) Next is the step of matching the person's performance characteristics with the performance standards and determining performance differences therebetween.

e) From the above information, the following step is to accomplish an identification of performance components of the performance differences, and ascertain any matchups of these with related skeletal and muscular components of the skeletal and muscular differences which would be accountable at least in part for the performance differences. There is also identified any non-matchups where the performance component or components do not at least in part relate to a corresponding physical component of physical differences as a means of ascertaining the following:
   i) performance differences not related primarily to either or both of skeletal or muscular differences;
   ii) performance differences related primarily to either or both of skeletal or muscular differences;
   iii) performance differences due to both the above.

f) When the above steps are accomplished, then either or both of two remedial courses of action can be implemented, namely:
   i) improving either or both of the skeletal and muscular characteristics of the person and/or;
   ii) improving the performance characteristics in accomplishing a task or tasks.

Other features will become apparent from the following detailed description.

BRIEF DESCRIPTION OF THE DRAWINGS

FIG. 3 is similar to FIG. 1, showing the back swing, down swing, and follow-through;

DETAILED DESCRIPTION OF THE PREFERRED EMBODIMENTS

Figure 1:
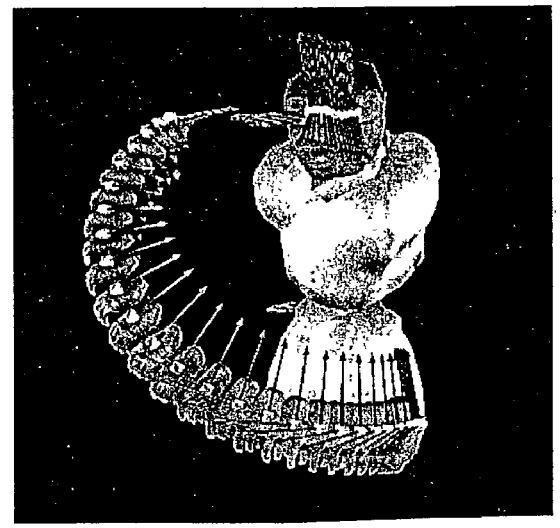
FIG. 1 is a graphic representation of the back swing accomplished in accordance with the present invention.

The system and method of the present invention comprises broadly six main components. These will be described below in sequence under appropriate headings:

a) Assessing, Evaluating, and Quantifying of a Person's Overall Physical Characteristics and Capabilities as they Relate to Generally his/her Physical Well-Being;

Reference is made to the attached twenty sheets entitled "Physical Therapy Initial Evaluation" numbered 1A–20A, which is one preferred form of a document that would be used in implementing this first component of the system of the present invention. To comment briefly on its contents, at the bottom of Page 1, there is indicated the beginning of the postural inspection, and this follows through on to Page 5. At the bottom of Page 5, there is listed the neurological tests, and following that on Page 6 and following are various special tests. For example, observations are made on weight distribution when a person is standing, and a functional squat. On Page 7 there begins joint and muscle palpitation testing and then segmental testing comprising cervical spine, thoracic spine, etc. From there, there is testing of flexibility in the shoulder, elbow, hip, knee, and ankle/foot. On Page 12 and following, there is the strength assessment. The summary sheets are on Pages 19 and 20.

Also, reference is made to attached pages 21A–24A, which is entitled, "Fames Clinic-Musculo Skeletal Evaluation", which is an updated summary sheet. The designations M.A.P. relates to posture. The term "3-D Spine" relates to spinal flexibility. Below that is, "Segmental Mobility" relating to how each vertebrae moves. The term "R.O.M." relates to shoulder motion and flexibility. In the middle of page 2, there is a term "flexibility", and listed below that, "hamstring-right", "hamstring-left", etc. relating to what is termed in physical therapy as the flexibility in the lower quarter of the person's body. On page 3, there is the testing of general strength and more specifically in the middle of page 3, grip strength, and below that overall lower body strength. Then at the bottom of page 3, there are some special tests relating to weight distribution and balance. A summary sheet is provided as page 4.

It is important to note that this information is gathered in such a way that it is quantified so that progress, lack of progress, and/or various changes can be monitored as the program progresses.

b) Utilizing the Information of Item (a) of Strengths, Deficiencies, and Areas of Desired Improvement or Correction Identified in Item (a) Above in Initiating Remedial Steps, and/or Steps for Improvement, Along with a Program for Accomplishing Certain Goals and Monitoring the Results.

This is accomplished at least in part in the use of the Physical Therapy Initial Evaluation Form discussed above. For example, in that form there are prescribed or indicated functional goals and/or treatment plans as various items are assessed. This overall process identifies the areas where the person either should seek improvement for maintaining proper well-being (e.g. alleviating potential back problems, or a set of exercises to minimize the probability of it occurring), or simply where a person may want to find improvement for his or her overall physical well-being.

This component of the present invention could apply to a wide variety of physical activities.

c) Conducting an Assessment and Analysis of one or More Specific Activities of a Person (e.g. an Aspect of an Athletic Performance), Initiating the Procedures to Improve such Performance, and/or Achieve Other Goals and Monitoring the Same as Part of an Ongoing Program;

It is believed that the various features of the present invention can be better understood by describing how the system and method of the present invention is applied to a situation where a person wants to improve his athletic performance, such as in the game of golf.

The first step is to obtain quantifiable information about the physical characteristics of the person relating to:

i) the person's physical characteristics, including skeletal characteristics, including flexibility and movement of the joints, and also the muscular characteristics, including movement, flexibility and strength of the various muscles in the person's body; and ii) the person's performance characteristics in performing the physical movements in a particular task or tasks, which in this case is the golf swing.

The primary apparatus used in accomplishing a substantial portion of the identification of physical and performance characteristics is already commercial available. In one such set of equipment, a plurality of sensors are placed on various places on a person's body. Each of these sensors is able to give information concerning the exact physical location of that sensor at any time, and also the angular orientation of that sensor.

In a preferred form of the present invention, four such sensors are used. In analyzing the person's golf swing, the first sensor is placed in the middle of a person's forehead, the second is placed at a location just below the back of the neck (i.e., the spine T-1 location) where there is a larger protrusion at the start of the spine, the third is positioned at the middle of a person's sacrum, which is on the back of the person just below the spine and just below the belt-line, and the fourth is placed on the middle of the back of the person's left hand (i.e., for a right-handed golfer). Data is taken by the apparatus at 120 readings (data points) per second. These data points are taken sequentially from the four sensors so that each sensor would have 30 data points per second. Thus, with each sensor reading not only location, but also orientation, and the velocity of the movement of the sensor can be ascertained by examining the spacing of the data points in determining the distance traveled in each 1/30 of a second time segment. Obviously, more sensors could be utilized if required, and also be placed at other locations.

Also, the velocity of the club head could be ascertained by using a fifth sensor on the club head, or it could also be ascertained by taking readings from a radar type apparatus.

Also, this same sensing apparatus can be used in ascertaining certain physical characteristics of the person relating to flexibility. This will be discussed later in this text.

Figure 2:
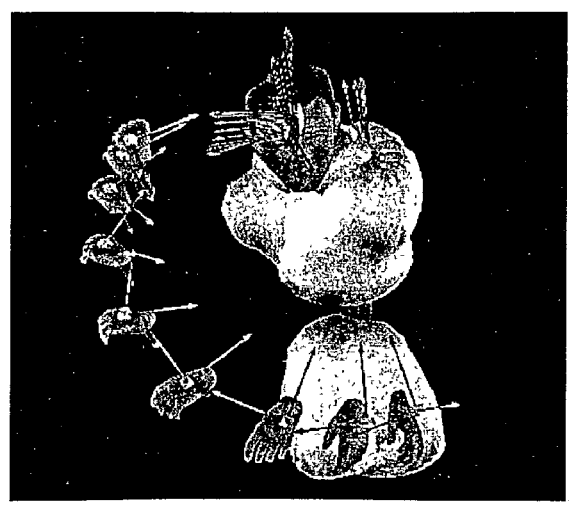
FIG. 2 is similar to FIG. 1, showing the down swing.
Figure 3:
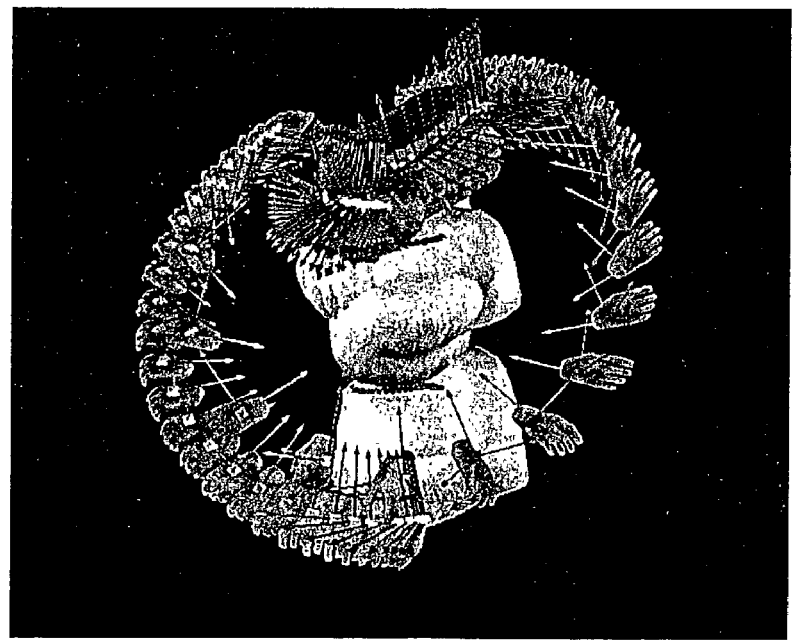

To illustrate how this data can be represented graphically by use of this apparatus, reference is now made to FIGS. 1–3, which show the movement of the left hand and also movement of the person's head. In FIG. 1, the person's left hand can be seen to move upwardly in the back swing motion. The closeness of the hand at each data point illustrates the relatively lower velocity. In FIG. 2, there is shown the movement of the left hand on the down swing, and the spacing of the hand at the data point illustrates the relatively high velocity of the movement of the hand. FIG. 3 shows not only the positioning of the left hand during the back swing and down swing, but also shows the movement of the left hand and the head during the follow-through motion after impact.

Figure 4A:
FIGS. 4A, 4B, and 4C are graphic representations similar to FIGS. 1, 2, and 3, but showing the full golf swing from a side view, bottom view, and top view, respectively.
Figure 4B:
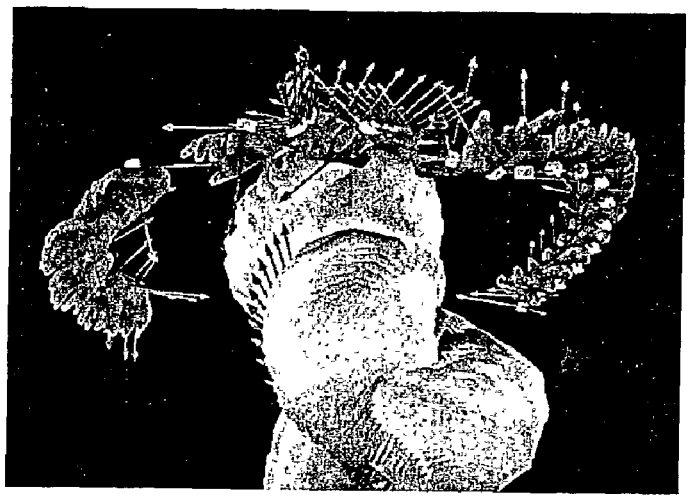
Figure 4C:
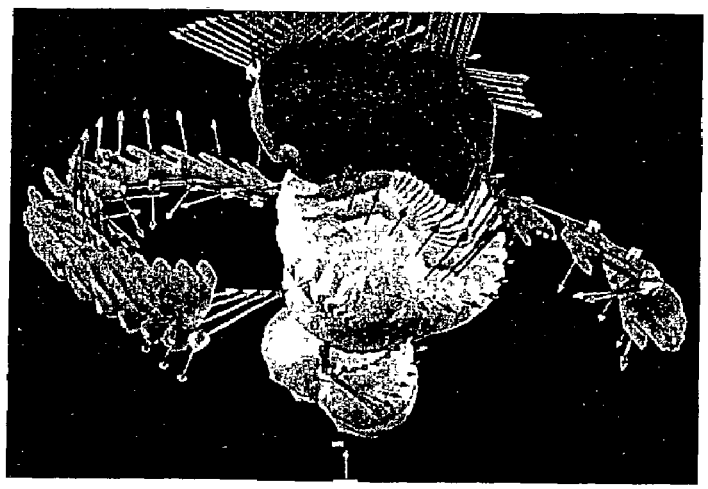

Then, FIGS. 4A, 4B, and 4C are illustrations similar to those shown in FIGS. 1–3, but taken from different views. FIG. 4A is a side view, FIG. 4B is a view taken from below the person, and FIG. 4C is a top view.

Figure 5A:
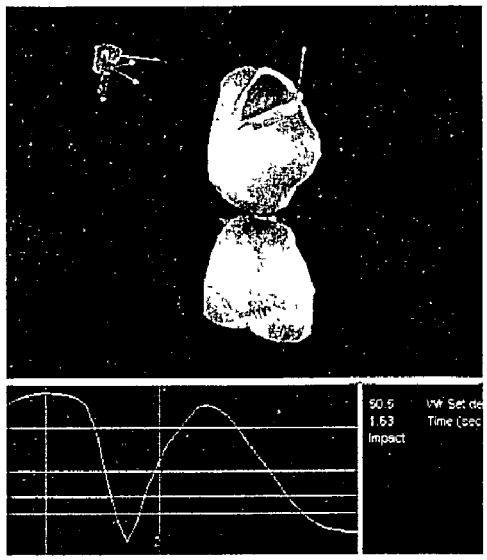
FIG. 5A is a graphic representation of a person's torso and left hand at the top of the back swing.
Figure 5C:
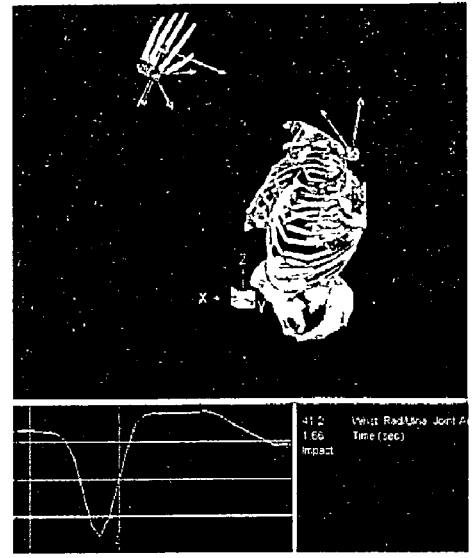
FIGS. 5C and 5D are similar to FIGS. 5A and 5B, respectively, showing another golf professional making a swing, with views being taken at the same locations as FIGS. 5A and 5B.
Figure 5B:
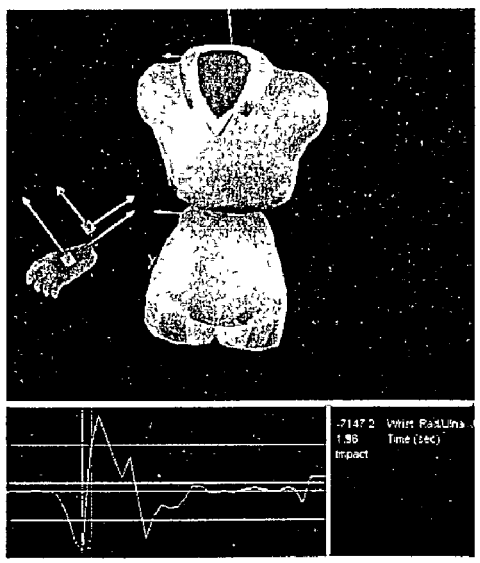
FIG. 5B is a view similar to FIG. 5A, showing the torso and hand at wrist release portion of the swing.
Figure 5D:
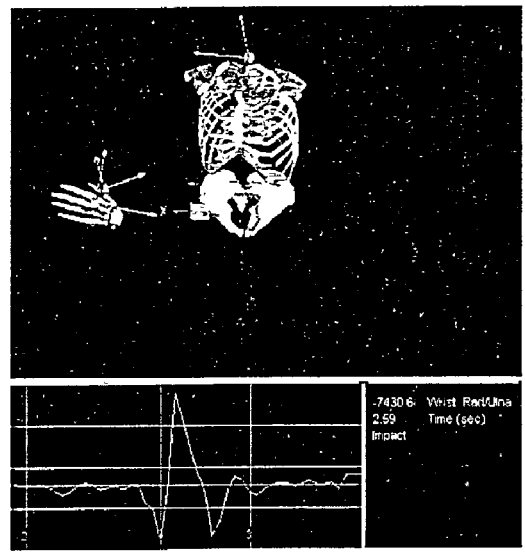

By way of further example, reference is made to FIGS. 5A through 5D. FIGS. 5A and 5B on the left hand side of the drawing show the position taken by a professional golfer at two locations, with the top left figure showing the location of the left hand and also the orientation of the body at the top of the back swing, and FIG. 5B showing the position partway through the down swing at the beginning of wrist release. FIGS. 5C and 5D are similar to FIGS. 5A and 5B, respectively, showing the movements of a second professional golfer.

Figure 6A:
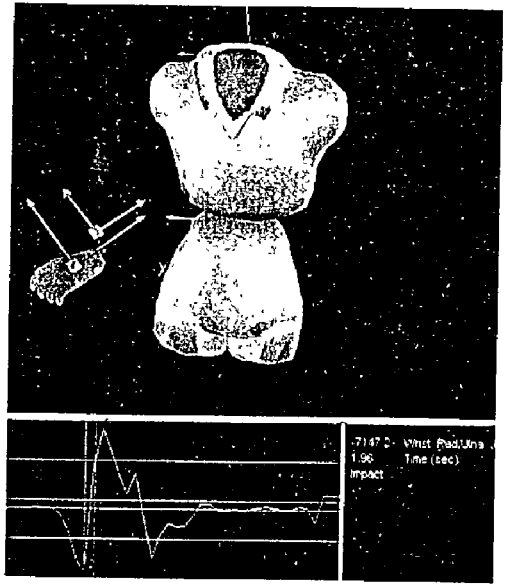
FIG. 6A is a view similar to FIG. 5A, but showing the position at wrist release.
Figure 6C:
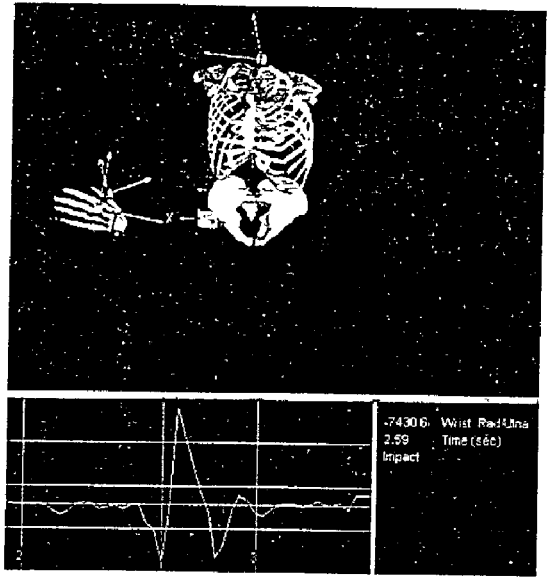
FIGS. 6C and 6D are similar to FIGS. 6A and 6B, respectively, but showing another professional golfer going through these motions.
Figure 6B:
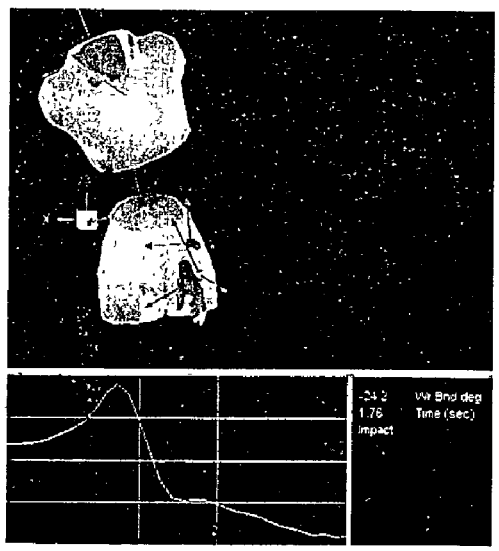
FIG. 6B is a view similar to FIG. 6A, but showing the person in that position at impact with the golf ball.
Figure 6D:
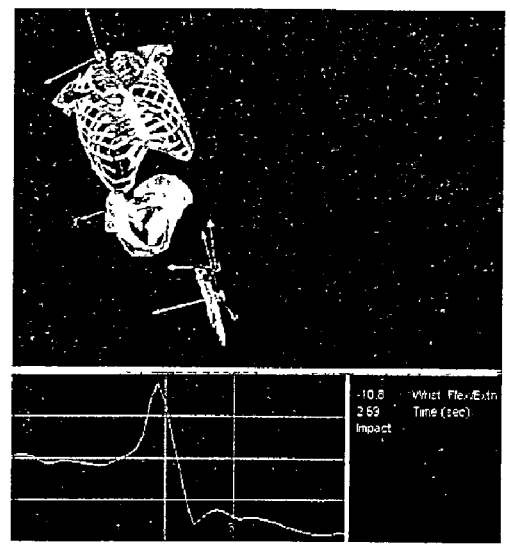

Reference is now made to FIGS. 6A–6D. FIGS. 6A and 6B shows the position of the golfer's left hand and body at an earlier point in the swing in lower left FIG. 6B at wrist release, and in the upper left FIG. 6A showing these positions at impact of the golf club with the golf ball. Similar representations are shown at FIGS. 6C and 6D, respectively, these taken of another professional golfer.

When the swing of a golfer is being recorded by this apparatus, the person is asked to do, for example, five swings with the driver and five swings with a drive iron. These would be averaged to ascertain what would be considered the person's normal golf swing. In some instances, one or two of the swings may follow a rather different path than the others, and this could be eliminated for purposes of obtaining this average. However, if there are these aberrations in the golf swing, this would indicate a lack of consistency in the swing.

With this information being gathered, then the person's golf swing could be evaluated and a comparison made with what would be a desired norm, which would be the "idealized" golf swing for optimum performance. In general, the golfer aims at accomplishing two things, namely, consistency and distance. The ideal swing which, in general, would give optimum performance has a basic foundation which is the correlated kinetic sequence in the swing. This involves movement of the person's hips, the movement of the shoulders, and the movement of the hands. This can be analyzed in terms of the sequence, acceleration, and the velocities.

Figure 7:
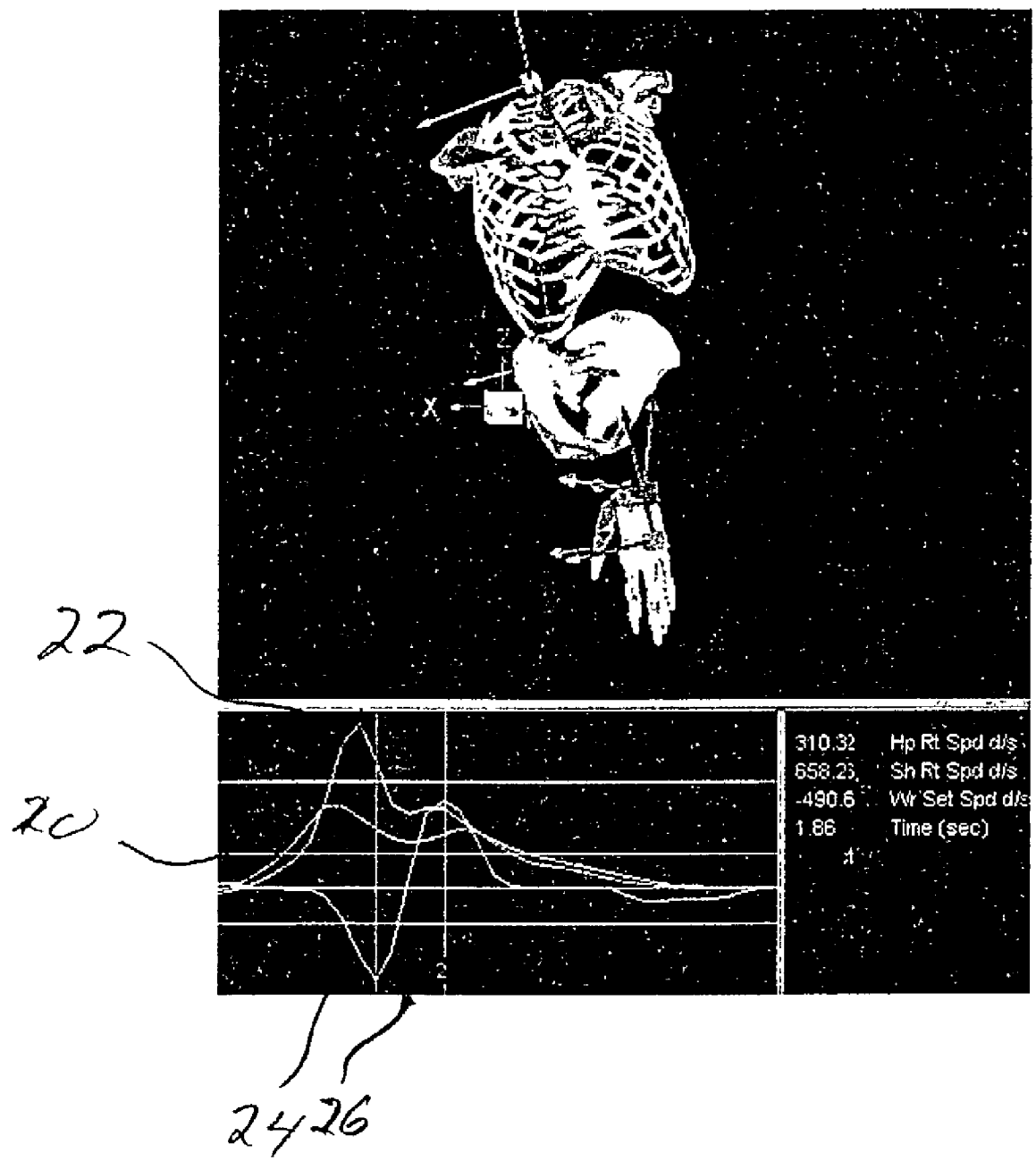
FIG. 7 is a view similar to FIG. 6D, showing the person's hand at or about the impact location, and at the bottom of FIG. 7 is a graph illustrating the velocity gradient of the hip movement, shoulder movement, and wrist breaking movement, plotted against time to illustrate the desired sequence in a golf swing.

The movement of the hips should reach a maximum velocity first, followed by the shoulder maximum velocity, and this being followed by the hand speed relative to the maximum hand velocity. With these being properly coordinated, this can be correlated to a "whip action". Reference is now made to FIG. 7 which shows the position of a golfer's body in an optimized swing at or very near to the point of impact. In the upper part of FIG. 7, there is shown the skeletal representation of the golfer and also the left hand of the golfer. In the bottom part of FIG. 7 there is a graph where the horizontal axis plots time, and the vertical axis plots velocity.

The curve 20 represents the velocity of the movement of the hips rotating through the swing, and it can be seen that the velocity of the hips becomes a maximum at an earlier time. Then, this is followed by curve 22 which indicates the velocity of the shoulders as these rotate, and it can be seen that this movement peaks out shortly after the velocity of the hips (curve 20) peaks out. Finally, there is the third curve 24 which shows the angular velocity of the wrist rotation. It should be noted that for clarity of illustration, this curve 24 is an inverse curve. It can be seen that the velocity of the curve 24 peaks out later than the peak velocity of the shoulders 22. The approximate location of the impact in terms of time is indicated at 26 on the graph. It will be noted that this point of impact is a very short time period subsequent to the peaking of the physical movement of the hand relative to the wrist. This can be attributed to the flexing of the club during the swing, and the action of the club being such that when the club is flexed, this energy stored in the club is now being translated into kinetic energy to maximize the velocity of the club at the location of impact.

The above discussion relating to the relative motion of the hips, shoulders, and hands, is what could be termed the "swing fundamentals" and these relate predominately to the movement of the hips, trunk, and shoulders. Then in building on these swing fundamentals, the next consideration is what could be termed "shot making" which involves more the movement of the arms, hand position on the golf club, etc. After the golf swing of the person has been analyzed, then this is compared to the idealized golf swing to determine the differences. Then an analysis needs to be made as to whether these differences relating the person's golf swing are due to the physical characteristics of the person making the swing or due to a "learned defect" in the golf swing. This leads us into another basic component of the system of the present invention, and that is the physical evaluation of the person. As indicated previously, this physical evaluation would relate primarily to the skeletal and muscular characteristics of the person.

Basically, the analysis of the person's physical characteristics is conducted in substantially the same way as indicated in Step a) which is listed in the next paragraph after the title, "Description of the Preferred Embodiments of the Present Invention", this relating to the assessing, evaluation, and quantifying of a person's overall physical characteristics and capabilities as they relate generally to his/her well-being. This is discussed shortly after that portion of the text, and reference is made to the attached twenty sheets entitled, "Physical Therapy and Additional Evaluation".

Let us look first at the skeletal characteristics, and (as indicated above) this relates essentially to joint movement and flexibility. As part of the skeletal evaluation, the same basic apparatus used in analyzing the golf swing can be used in this evaluation of a person's skeletal characteristics. In this instance, three of the four sensors would be placed at the same locations as described above relative to analyzing the swing, namely placing the first sensor on the forehead, the second sensor at the top of the spine (the T-1 location), and the third sensor on the sacrum. However, instead of placing the fourth sensor on the back of the left hand, this fourth sensor is placed between the second and third sensor at the T-12 location on the spine.

With these sensors in place, the person is asked to go through various physical movements. The person's feet are placed a medium distance apart, and the person is asked to move the shoulders in a twisting motion right and left, and also forward bending, back bending, and side bending. In like manner, the person is asked to move his/her head in a twisting motion, forward and back motions, and also side-to-side motions. Then, the rest of the physical analysis and assessment proceeds as indicated earlier in this text, as outlined in the attached pages 1–24.

After the physical analysis and assessment is conducted as indicated above, then this is matched with desired norms relating to skeletal and muscular characteristics and deviations or differences from a person's skeletal and muscular characteristics are identified. These desired norms are established in large part to the more general physical characteristics. In addition, these physical norms could be made somewhat more specific relative to the golf swing.

The next step is to correlate the differences noted in the person's golf swing relative to the idealized golf swing, with the person's skeletal and muscular differences from the desired physical norms.

In noting these differences, there will be performance components of the performance differences which should be matched with related skeletal and muscular components of the skeletal and muscular differences of the person from the idealized norm, and these are matched to see where the performance components are at least in part related to the corresponding physical difference components.

It could be, for example, that due to physical limitations (e.g. stiffness in certain joints), the person is compensating for this stiffness in the golf swing. For example, it could be that in the back swing where the person is raising his club from the address position, at the top of the swing there may be a straightening of the person's right knee at the top of the back swing. This could possibly indicate a restriction in the right hip (for the right-handed golfer), not allowing him to rotate over the top of his right hip.

As an example of another compensation, a person may have what is termed an "over the top" swing, where the person pulls down with his arms to a greater extent and not allowing the hips and spine to rotate appropriately. This can be seen with limitations in the spine or spinal restrictions.

Once these relationships or matchups are established (i.e., certain physical characteristics that depart from the norm relative to differences in the golf swing from the derived norm), either or both if two courses of action can be implemented. The first would be to improve the skeletal and/or muscular characteristics of the person to come closer to the desired physical norm, so that the more idealized golf swing can be achieved. This could involve flexing stretching exercises for certain joints and exercise to strengthen and obtain the flexibility in the muscles.

It should be noted at this time that initiating such improvements in the person's skeletal/physical capabilities has a fringe benefit over and above enabling the person to improve his golf game. When the skeletal joints of the person are functioning with sufficient flexibility and range of motion, there is an optimized balance for each joint functioning as it was intended. However, if some of the joints are stiff, then other joints may have to compensate for this. For example, let us assume that some of the vertebrae in a person's back are stiff and we look at five joints that are each supposed to rotate through ten units of rotation to obtain a total rotation of fifty units. If each joint is rotating ten increments, then they are rotating within the range of their flexibility. However, let us assume that some of the joints are only operating at four or five units, and the fifth joint is rotating at a greater degree to compensate to this, for example, like twenty units of movement. This is bad for all of the joints. The joints which are not getting sufficient movement will deteriorate because of this lack of movement. On the other hand, the joint which is being rotated to twenty units of rotation could be over-stressed, and this also would lead to deterioration.

This is also true of muscular flexibility. For example, if certain muscles are stiff to restrict a person's motion, then that will reflect on other portions of the body. An example of this, is that the flexors that are the top of a person's leg sometimes become stiff, and this limits the movement of the legs in a rearward direction. For certain movements, the person would compensate for this by causing a greater backward bending of the spine beyond which would be beyond what is desired.

The other course of action is where a person does not really want to take the trouble to improve his/her skeletal/muscular characteristics, but simply wants to optimize his/her golf swing, recognizing that he/she has certain limitations which would make his/her swing depart from the desired norm. In this instance, there may be an adjustment of the person's golf swing, taking into consideration the physical limitations of the person. In some instances, it would be desirable, for example, for the person to shorten the back swing and possibly make other adjustments in the swing.

If the system of the present invention were to be used in an idealized situation, then there would be three main building blocks which could be envisioned to be in the shape of a pyramid, with the broader base of the pyramid relating to the evaluations of the person's skeletal/muscular characteristics and the improvement of these toward the optimum. The second middle part of the pyramid would relate to the swing fundamentals, which predominately involves the positioning and the relative movements of the head, trunk, hips, and shoulders. Finally, at the top of the pyramid, there is the "shot making", which is refining a person's golf swing.

However, it quite often happens that the person is more motivated toward making the improvement in the golf swing, and wants to make this a priority but still wants improvement of physical characteristics. In this case, the analysis of the golf swing and the program to improve the person's physical characteristics can proceed simultaneously. For example, if a person would want a program involving eight weekly sessions where he/she would come in once a week, the instructor would work on a person's golf swing, along with his/her physical limitations. At the same time, the person would be motivated to do at least a certain amount of exercise (i.e., flexibility, strength, or both).

In this eight-week session, the practitioner/physical therapist who is using the program of the present invention, would be able during these eight-week sessions to have a reasonable assessment of the person's physical limitations, such as stiffness in certain areas of the body and possible improvements on the same, and as the practitioner/physical therapist does so, he could be making the appropriate adjustments in the golf swing, as well as taking part of this time to bring the person along in a physical improvement program of skeletal/muscular capabilities.

After the fundamental swing is established and the person's related physical characteristics are identified and quantified, then the person may wish to sign up with a golf professional to continue the golf instruction. In this instance, there would desirably be a consultation between the golf professional who would continue teaching the person, and the practitioner who is practicing the present invention, so that the golf professional is aware of the limitations which have been ascertained and quantified. Thus, the golf professional would be better able to optimize the person's swing within the scope of the physical limitations.

To comment further on the present state of the art and improving a person's golf game, it can sometimes happen that when a person goes for a golf swing, the golf professional may recognize that the person might be there only for possibly three lessons. Accordingly, within that shorter time frame, the golf professional will make adjustments which could be made more quickly and easily. For example, he may simply make adjustments in the golf grip or certain mechanics of the swing.

Let us now take the situation where the person has dedicated himself to a long-range plan to improve not only his/her performance in his/her golf game, or possibly some other sport, but also to continue with the program for overall physical well-being. In this instance, from time to time (e.g. annually or semi-annually or more often), the overall evaluation of the person could be repeated to see what improvements or other changes have been made in the person's skeletal/muscular performance, and also relate this to the person's sport activity (e.g., the golf swing). It could be that the physical improvements made by the person in, for example, flexibility or strength of certain regions of the body, would enable the person to make further adjustments in the golf swing for further consistency and/or distance.

Another important aspect of the present invention, is that all of these factors of a person's physical characteristics and physical performance are quantified. If a person is advised of the areas of deficiency where improvement is especially needed, then the person would be better able to focus his/her efforts in those areas. For example, it may be that a person's physical strength is quite adequate for properly performing daily tasks or some sports activities, but the skeletal and muscular flexibility is lacking. In that case, if the person has, as a practical matter, only so much time to devote to improving the overall physical well-being and performance in certain sports activities, the person would be guided in how to focus his/her efforts more productively within the limitation of the time to devote to the self-improvement program.

d) As Part of Initiating the Procedures of Item (c) Above Reviewing the Assessment and Analysis of the Specific Movements of the Person (as Specified in Item (c) Above) to the Information of the Basic Physical Characteristics and the Abilities and/or Deficiencies of the Person, as Specified in Item (a) Above, as a Means of Improving Performance.

As indicated above in Section C, the golf swing which functions rather well for Tiger Woods, may not be the same type of swing that should be adopted by a middle-aged golfer lacking Tiger Woods' power and flexibility. Also, the "optimized swing" is not necessarily the same for all golfers.

For example, if one views the golf swing of Arnold Palmer in his prime, one can see a somewhat different style than other quality professionals of the same vintage, or for that matter, today's quality golfers.

Thus, in the system of the present invention, there needs to be the analysis of the person's physical characteristics relative to an optimized swing for that person. The flexibility of the person in certain portions of the body and also the strength of various muscles could be reviewed to inject these into the equation to lead to the improved golf swing. Since this is discussed above in Section C, this will not be described further in this section. Now for yet further improvement in the golf swing, we are brought to the next subject.

e) From the Assessment of Item (a) and from the Program of Item (c), and Item (d) Identifying Possible Additional Remedial Steps and/or Remedial Program Relating to Physical Characteristics and/or Deficiencies to Achieve Improvement of (and/or other Goals Relating to) the Performance of the Physical Activity or Activities of Item (c).

As described above in Section C, when the golf swing is matched with the person's physical characteristics and abilities, then the characteristics and capabilities could be evaluated against certain norms or desired levels to see if improvement in the person's physical abilities could be made to improve performance. For example, the person's grip in the left hand could possibly be strengthened so that better control or action of the driver could be achieved. Also, it should be recognized that in combing these various elements, these may not necessarily occur in the same order, and they may be going on simultaneously.

In general, the overall assessment of the person's physical characteristics and strengths (item (a) above) would usually be done first. This would be of value not only for analyzing particular actions sports activities, but for a number of other purposes relating to overall physical well-being as indicated previously. Second, there is obtaining data on the person's golf swing so that the mechanics of the swing could be analyzed. Third, there is the matching of the person's golf swing to the particular physical strengths, weaknesses, and characteristics of that person to arrive at the swing suitable for that person (item (d) above). Fourth, the further analysis could also explore the possibility of somehow improving the person's physical capabilities so that there could be further optimization (item (e) above). This could relate to such things as being more limber in certain respects, strengthening certain muscles to obtain a better balance, etc. This could relate back to certain repeats of item (a) to monitor progress in the physical improvement. This is to give one example of how the components can be used to achieve a rather specific goal.

To give a further example of the data that could be gathered to analyze a person's swing, there is enclosed a data sheet, identified in pages 25A–27A, entitled "Swing Analysis." In the far left-hand column there is listed the movement which is being monitored, such as hip rotation, right and left shoulder rotation, etc. Then there are four stages of the swing listed, namely the address, the top of the swing, the swing at impact, and finally the finish of the swing. In the first two columns under each category, the ranges of an optimized swing for a professional golfer are given, and in the third column, there are inserted the value which is recorded in analyzing the person's swing. In this particular example, the values for the golfer being analyzed are not shown.

In the above example, there has been a discussion only of analyzing the particulars of a golf swing. It is readily apparent that this same type of analysis could be made with regard to other motions in athletics such as a backhand in tennis, punting a football, in basketball shooting a free throw or a jump shot, pitching a baseball, passing a football, etc.

Further, certain repetitive athletic movements could be analyzed and monitored, such as running. A runner may be bothered by Achilles tendon problems or shin splints. The person's stride could be analyzed and it may be that certain remedial steps could be taken in the manner in which the person runs. In other instances, this may call for further analysis of the sort of footwear the person has, the foot support the person has in the shoe, etc. Also, it may be that certain exercises related to strength and flexibility would enable the person's running stride to be such that these ailments could be alleviated.

f) Relating the Components Identified as Items (a) through (e) so that these are Combined in a Manner to become Part of an Overall Pattern of Living.

This is part of the system where we "put it all together", and in terms of overall social valve this may well be the most important aspect of the present invention. Let us begin by placing this program of optimizing physical well-being back into the broader perspective of the person's overall well-being. Previously in the introductory portions of this text, personal well-being is segmented into five categories, namely (a) basic health care, (b) adopting good health habits, (c) proper diet, (d) mental, emotional, psychological and spiritual well-being, and finally the subject matter of the system of the present invention, namely (e) physical activities and condition.

As indicated earlier in this text, when a person is working towards making an improvement on all of these five areas of his or her life which make up a large part of the total package of personal well being, these work synergistically in that as a person becomes active and/or makes improvement in one area, there is a "ripple effect" where it acts as a stimulus to make improvement and/or maintain well being in the other areas.

To focus on the aspect of this "ripple effect", as indicated above, the fourth broad category of overall personal well being is the mental, emotional, psychological and spiritual well being where the person has the goals of his/her day to day living in order. Using this as a springboard, the person can then make it one of his/her goals to add a program of physical activity and conditioning into the lifestyle, and as part of this also participating in certain sport or recreational activities. If this is done, it will likely turn out that the benefits of these physical activities will operate synergistically with the person's goal in mental/psychological well-being. As the program for the person's physical well being and the physical activities related thereto continues on through not just on a month to month basis but a year to year basis, this will make a contribution to the person's overall outlook on daily living. It is not just a matter of physical health and fitness, but also of recreation, enjoyment of physical activities, and even a strong element of social activity by interacting with other people in these activities.

In viewing the system of the present invention and analyzing all of its components, it becomes apparent that one of its main functional advantages is that it is in a sense "all encompassing", achieved by putting all the loose ends and fragmented information into a unified system. It begins by a basic assessment of the person's overall physical characteristics, strengths, deficiencies, etc. and quantifying these. Then there is a more general program for basic improvement, regardless of how this would relate to any specific activities. Then within the framework of the system the person will be able to set some specific goals (e.g. a more consistent golf swing), and hopefully these will be long range goals, not just to obtain a single skill in one isolated activity, but to put it together in a pattern of living.

Also, these do not have to be highly ambitious goals. For example, let us take the subject of cardiovascular fitness. In the early part of the decade of the 1960's Doctor Cooper published his books on "aerobics" and motivated many millions of people into a program of cardiovascular fitness. In his more recent book on "The Anti-oxidant Revolution", as a result of many years of research concluded, it appears that in order to obtain the cardiovascular benefits of exercise, only a relatively modest amount of cardiovascular exercise is required. He further points out that if a person is going to embark on a very ambitious program of cardiovascular exercise, he or she should consider the stress this places on the body and incorporate into his or her diet the anti-oxidants to balance this out. He also indicates that in his personal life, he has a more ambitious cardiovascular aerobic exercise program, and he does this more for his sense of physical well-being than for cardiovascular benefits. This is an example of setting either modest goals or more ambitious goals. Both can fit into the system of the present invention.

To look at the system of the present invention possibly from another view, it can be considered as having more or less of a rather basic framework which relates to the basic physical health and fitness of the person in all aspects (cardiovascular, appropriate physical strength, limberness and agility, avoiding aches and pains, etc.) and also a program to maintain and/or improve these more basic goals. Then with this established as a foundation, then the person can at the same time move into working toward more specific goals, and the example given prior to this is solving problems in the person's golf game or some other sports activity, whether it be league basketball, tennis, water skiing, mountain biking, etc. Then all of this is related back to the basic of evaluation, and also quantifying the various characteristics and capabilities of the person's body.

Then again, at the risk of being repetitious, it should be stated that in accomplishing all of these goals, relating to the person's physical activities and condition, this will enhance the other aspects of a person's life and lead toward overall well-being.

It is to be understood that the above examples are given simply as specific applications, and the system of the present invention is not to be limited toward those particular examples. Also, there are various additional activities which would come within the system of the present invention, and various modifications could be made and still be within the scope of the broader concepts incorporated herein.

We claim:

1. A method of improving either or both of physical well-being and physical performance of a person, said method comprising:
    a) ascertaining quantifiable information about the person's characteristics relating to:
        i) the person's skeletal characteristics, including flexibility and movement, and muscular characteristics including movement, flexibility, and strength;
        ii) the person's performance characteristics in performing physical movements in performing a task or tasks;
    b) establishing performance standards corresponding to a desired performance level for said task or task, and also establishing skeletal and muscular standards corresponding to desired skeletal and muscular characteristics capable of matching said performance standards;
    c) matching the person's skeletal and muscular characteristics with the skeletal and muscular standards and determining skeletal and muscular differences therebetween;
    d) matching the person's performance characteristics with the performance standards and determining performance differences therebetween;
    e) accomplishing identification of performance components of the performance differences, and ascertaining any matchups of these with related skeletal and muscular components of the skeletal and muscular differences which would be accountable at least in part for the performance differences, and also identifying any non-matchups for the performance components that do not at least in part relate to corresponding physical components, as a means of ascertaining;
        i) performance components of performance differences not related primarily to either or both of skeletal and muscular components of the skeletal and muscular differences, or both;
        ii) performance components of the performance differences relating primarily to either or both of skeletal and muscular components of the skeletal and muscular differences;
    whereby it becomes possible to identify performance components relating to differences from actual performance and desired performance standards which performance components can be correlated with information relating to skeletal and muscular components of skeletal and muscular differences from a desired standard, and also possible to identify performance components of performance differences that do not primarily relate to skeletal and muscular components of differences, thus better enabling identifying a selected remedial course or courses.

2. The method as recited in claim 1, further comprising developing either or both of:
    a) a remedial course comprising either or both of:
        i) improving either or both of skeletal and muscular characteristics of the person;
        ii) improving learned faults and/or aberrations in performance characteristics of the person.

3. The method as recited in claim 2, wherein the physical performance which is to be improved is a person's golf swing, said method comprising recording for analysis relative positions of the person's hips, torso, arms, and at least one hand during the swing, for performing an assessment of the person's skeletal and muscular characteristics, ascertaining differences in the person's golf swing relative to an idealized golf swing, also ascertaining skeletal and muscular characteristics of the person having skeletal and muscular components relating to the differences in the person's golf swing relative to the idealized golf swing, and initiating a course of action to accomplish either or both of:
    i) making physical improvements to the person to reduce the skeletal and muscular differences that relate to the differences of the golf swing, or both skeletal and muscular differences; and
    ii) modifying the person's golf swing to better match the skeletal and muscular characteristics of the person that relate to the golf swing.

* * * * *